United States Patent [19]
Palmer et al.

[11] Patent Number: 5,959,173
[45] Date of Patent: Sep. 28, 1999

[54] HYBRID SEED PRODUCTION

[75] Inventors: Thomas Pattinson Palmer; Anthony John Conner, both of Christchurch, New Zealand

[73] Assignee: Her Majesty The Queen in Right of New Zealand, c/o Dept. of Scientific and Industrial Research, etc., Canterbury, New Zealand

[21] Appl. No.: 07/552,880

[22] Filed: Jul. 16, 1990

Related U.S. Application Data

[63] Continuation-in-part of application No. 07/222,616, Jul. 21, 1988, abandoned.

[30]  Foreign Application Priority Data

Jul. 30, 1987 [NZ] New Zealand ............................ 221267
Aug. 7, 1987 [NZ] New Zealand ............................ 221375

[51] Int. Cl.$^6$ ..................................................... A01H 1/00
[52] U.S. Cl. ............................ 800/273; 800/271; 800/266
[58] Field of Search .................................. 47/58, DIG. 1, 47/56.7; 800/205, 200, 230, 273, 271, 266

[56] References Cited

U.S. PATENT DOCUMENTS

| 4,517,763 | 5/1985 | Beversdorf et al. | 47/58 |
| 4,658,084 | 4/1987 | Beversdorf et al. | 47/58 |

OTHER PUBLICATIONS

Vasil. (1988) Biotechnology vol. 6 pp. 397–402.
Poehlman (1987) *Breeding Field Crops* AOI Publisher West Port CT. pp. 129–134.

*Primary Examiner*—Gary Benzion
*Attorney, Agent, or Firm*—Ross, Ross & Flavin

[57] ABSTRACT

The invention relates to improved methods of hybrid seed production. More particularly it relates to the use of one (or two) phytotoxic chemical resistant genes in the male (and female) parent in a hybridization process, followed by uncontrolled pollination and dosing the resultant hybrids with the one (or two) phytotoxic chemicals to eliminate plants arising from unwanted contaminating seeds and thus producing pure $F_1$ hybrids.

27 Claims, 2 Drawing Sheets

HYBRID SEED PRODUCTION

This is a continuation-in-part of application Ser. No. 07/222,616 filed Jul. 21, 1988 now abandoned.

FIELD OF INVENTION

This invention relates to an improved method of hybrid seed production. More particularly it relates to the use of a phytotoxic chemical resistant gene in a male parent in a hybridisation process followed by dosing of the resultant hybrids with the phytotoxic chemical to eliminate plants arising from unwanted contaminating seeds.

DESCRIPTION OF PRIOR ART

For the commercial production of hybrid seed the male and female parents are generally planted in an alternating pattern and seed is harvested off only the female parent. A major problem during hybrid seed production is to ensure that all of the pollen fertilising the female parent originates from the male parent. Seed arising from any other source of pollen will contaminate the hybrid seed population. Potential sources of contaminating pollen are pollen from the female parent, causing self pollination, or pollen from a neighboring field.

There are 6 ways of eliminating fertile pollen from the female parent (Simmonds, *Principles of Crop Improvement*, 1979):

1. mechanical (e.g. tomatoes)—hand emasculation of the female parent, followed by pollination;
2. dioecy (e.g. spinach)—removal of the male plants of the genotype from which seed will be harvested from a crop with separate male and female parents;
3. self incompatibility (e.g. brassicas)—interplanting of two self incompatible but cross compatible parents and harvesting of all seed, or use of a self incompatible genotype as the female parent with a self compatible pollinator and harvesting the seed from the female parent only.
4. nuclear male sterility (many crops) segregating female parent for male sterility (ms ms) and fertility (Ms ms); removal of male fertile plants and pollination of male sterile plants with pollen from the male parent (Ms Ms),
5. cytoplasmic male sterility (e.g. onions)—use of male sterile lines as the female parent, and
6. chemicals:
   (a) male gametocides (e.g. wheat)—spraying of female parents with a chemical that induces male sterility;
   (b) sex reversal (e.g. curcurbits)—spraying of female parents with plant hormones to revert male flowers into female flowers.

However there are several problems associated with such approaches:

(1) The physical separation of the female and male parents into alternating blocks in the field does not facilitate the efficient transfer of pollen from male to female parents and can result in less than maximum hybrid seed production.

(2) None of these approaches can guarantee the absolute elimination of fertile pollen from the female parent (and thus self pollination of the female parent). There are 2 components in this:

(a) Human errors can occur during hand emasculation and removal of male fertile plants when using dioecy and nuclear male sterility. Furthermore the labour involved in these practices is very costly.

(b) When using chemical sprays to control sex expression it is difficult to obtain an even application to totally prevent pollen production by female parents. Furthermore there can often be instability associated with the expression of self-incompatibility and male sterility genes. For example, it is known that elevated temperatures or high humidity reduce self-incompatibility resulting in a high proportion of self-pollinated seed, especially in brassicas (Frankel and Galun, *Pollination Mechanisms, Reproduction and Plant Breeding* (1977)). This has resulted in the release of a number of "rough hybrids" containing many self-pollinated plants (Simmonds). Fertility restoration in certain male sterile lines of onions has made it uneconomical to produce hybrid seed from otherwise excellent crosses (Grant, Onions, *Plant Breeding in New Zealand* (1983)).

3. In an attempt to circumvent foreign pollen contamination from a neighbouring field, hybrid seed blocks are grown in isolation plots. Recommended isolation distances vary from crop to crop depending on its mode of pollinations, and may range from 200 m in sorghum, corn and wheat, up to 6.4 km in sunflowers (Wright, Commercial Hybrid Seed Production, *Hybridisation of Crop Plants* (1980)). Attempts are made to remove all sources of contaminating pollen within these distances.

A solution to problem (1) above has been proposed in U.S. Pat. Nos. 4,517,763, 4,658,084 and 4,658,085 (all to Beversdorf et al).

All involve creating in the same female parent a combination of cytoplasmically inherited male sterility and either cytoplasmically inherited herbicide resistance (U.S. Pat. No. 4,517,763) or homozygosity for a dominant nuclear inherited herbicide resistant genes (U.S. Pat. No. 4,658,084). The concept allows the random mixing of the 2 parents for hybrid seed production, thereby aiding pollen transfer from the male to the female parent.

When the female parent is male sterile and herbicide resistant and the male parent is male fertile and herbicide sensitive, the seed produced from such plants can be of 2 types:

(1) True hybrid seed from the female parent (herbicide resistant); and
(2) Non-hybrid seed from self pollination of the male parent.

The non-hybrid seed resulting from the self-pollination of the male parent can be eliminated by spraying with the herbicide either after pollination but before seed harvest (thereby killing the male parent), or after sowing seed from the bulk harvest (thereby killing the non-hybrid seedlings after germination). This source of non-hybrid seed does not arise in standard hybrid seed production since in standard hybrid seed production the female and male parents are physically separated into alternating blocks in the field, and seed is only harvested off the female blocks. Hence production of a non-hybrid seed component is an inherent part of these patents due to the mixed sowing of the two parents.

Also claimed in U.S. Pat. Nos. 4,658,084 and 4,658,085 is the use of resistance to two different herbicides to allow the mixed random planting of the cytoplasmic male sterile female parent, its maintainer line, and the male parent. Plants from the maintainer line and non-hybrid seed from self pollination of the male parent are eliminated by their sensitivity to different herbicides.

A possible solution to problem 2(a) above has been prepared by Wiebe (A proposal for Hybrid Barley, *Agronomy Journal* (1960)).

Wiebe suggests the possible finding of a close linkage between the male fertility gene and susceptibility to a phytocide (DDT).

This allows the early identification of male fertile plants (Msms) in populations of female parents that segregate for male fertility (Msms) and male sterility (msms) when using nuclear male sterility. Such plants can therefore be removed from the female parent population prior to flowering and possible release of pollen that may lead to selfing of the female parent.

An identical proposal was suggested by European Patent Application No. 86104213.3 (Advanced Genetic Sciences Inc). However, this approach involves the random introduction of marker genes via transformation into the genome of male fertile plants (MsMs or Msms), and many independently transformed plants are genetically analysed to find an individual with tight linkage between the marker gene and the male fertility locus. Particular emphasis is placed on the use of suicide genes that will result in sensitivity to certain chemicals. The fertile plants can then be eliminated by a simple chemical spray at the seedling stage.

However the four above described patents still retain all the problems associated with contamination by foreign pollen, and contamination by self-pollination of the female parent due to a breakdown in male sterility (problems 2(b) and 3 above).

BRIEF SUMMARY OF THE INVENTION

It is an object of this invention to overcome both the above described disadvantages of the prior art. This and other objects of the present invention will be apparent to those skilled in the art from a reading of the following descriptions, examples and claims.

The present invention provides a method of forming a substantially pure $F_1$ hybrid population of plants, said method including:

(a) planting alternating plots of male and female parent plants;

(b) allowing fertilization of said female plants to occur; and (c) harvesting fertilised seed from said plots of female plants only; wherein the improvement comprises:

the male parent plants being resistant to a phytotoxic chemical, said resistance being attributable solely to a homozygous dominant nuclear marker gene, said resistant gene being absent from said female parent plants; and the method includes the step of:

(d) dosing fertilised seed harvested in step (c) with the phytotoxic chemical.

Step (d) may be carried out either before planting or after emergence of the seedlings. The phytotoxic chemical thus eliminates plants resulting from self-pollination of the female parent or foreign pollen sources and thereby achieves a substantially homogeneous $F_1$ hybrid population.

The above method may preferably be used for species of plants where both parents are self-compatible, or where one parent only is self-incompatible.

Preferably said phytotoxic chemical is a herbicide of any class. Alternatively, said phytotoxic chemical is an antibiotic, preferably kanamycin (an antibiotic complex produced by *Streptomyces kanamyceticus*).

The present invention further provides a method of forming a substantially pure $F_1$ hybrid population of plants in which both parents are self-incompatible or self-compatible, said method including:

(a) planting either alternating plots or a random mixture of first and second parent plants, the first parent plants being resistant to a first phytotoxic chemical and having a homozygous dominant nuclear marker gene absent from the second parent plants, the second parent plants being resistant to a second phytotoxic chemical and having a homozygous dominant marker gene absent from the first parent plants;

(b) allowing fertilization of the first and the second parent plants to occur;

(c) harvesting fertilized seed from the first parent plants and the second parent plants;

the second parent plants being resistant to a second phytotoxic chemical, said resistance to said first or second phytotoxic chemicals being attributable in each plant solely to a homozygous dominant nuclear marker gene, said gene resistant to said first chemical being absent from said second parent plants and said gene resistant to said second chemical being absent from said first parent plants; and the method includes the step of:

(d) dosing the harvested fertilized seed with both the first and the second phytotoxic chemicals.

Step (d) may be carried out either before planting or after emergence of the seedlings, to eliminate plants resulting from self-pollination of either said first or second parent plant or from foreign pollen sources. A substantially homogeneous $F_1$ hybrid population is thereby achieved.

Preferably the first and second phytotoxic chemicals are herbicides of any class.

Alternatively the first and second phytotoxic chemicals are antibiotics, preferably one said antibiotic is kanamycin.

Preferably, nuclear marker genes are inserted by a plant transformation technique.

Preferably the plant transformation technique used is Agrobacterium-mediated transfer.

Some aspects of Agrobacterium-mediated transfer of genes into plants are disclosed in European Patent Application No. 116718 (P. Zambryski); and European Patent Application No. 84116036.9 (Plant Genetic Systems N.V., p3, line 33); or cited in European Patent Application No. 861042133 (column 16, line 37).

Alternatively said plant transformation technique is direct DNA uptake transformation (into protoplast or cells, plant tissues or inflorescences).

In another possible method said nuclear marker gene is selected in a somatic cell culture. The patents to Beversdorf et al refer to such a method. In a still further possible method said nuclear marker gene is selected in a transfer protoplast fusion. In yet another possible method said nuclear marker gene is selected after inducing plant mutagenesis. Alternatively said nuclear marker gene is present by selecting a male or first or second parent plant having the desired gene.

The present invention further provides a method of testing the purity of $F_1$ hybrid populations of plants in which both parents are self-compatible or one parent is self-incompatible, said method including: carrying out the steps (a) to (c) of the first above described method; planting a small quantity as a sample of said seeds; dosing the seedlings after emergence with said phytotoxic chemical; and determining the percentage of seedlings resistant to said phytotoxic chemical.

The present invention further provides a method of testing the purity of $F_1$ hybrid populations of plants in which both parents are self-incompatible, said method including: carrying out the steps (a) to (c) of the second above-described method; planting a small quantity as a sample of said seeds; dosing the seedlings after emergence with the first and the second phytotoxic chemicals; and determining the percentage of seedlings resistant to the first and the second phytotoxic chemicals.

DETAILED DESCRIPTION OF THE DRAWINGS

Figure 1:
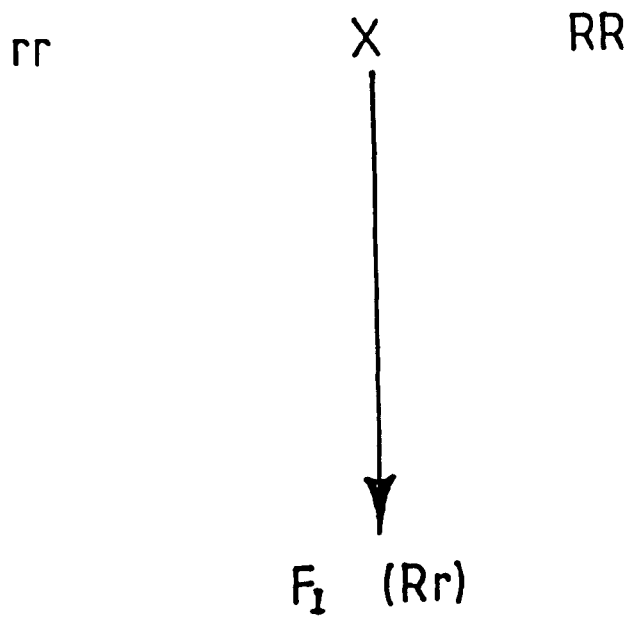
FIG. 1A is a diagrammatic representation of inheritance of resistance to a phytotoxic chemical in relation to hybrid seed production with the production of a true hybrid seed (Rr) being represented by the illustrated path, according to a first embodiment of the invention.
FIG. 1B is a diagrammatic representation of inheritance of resistance to a phytotoxic chemical in relation to hybrid seed production, with a representation of the seed being produced by the contaminating pollen (rr), according to the first embodiment of the invention.
Figure 1:
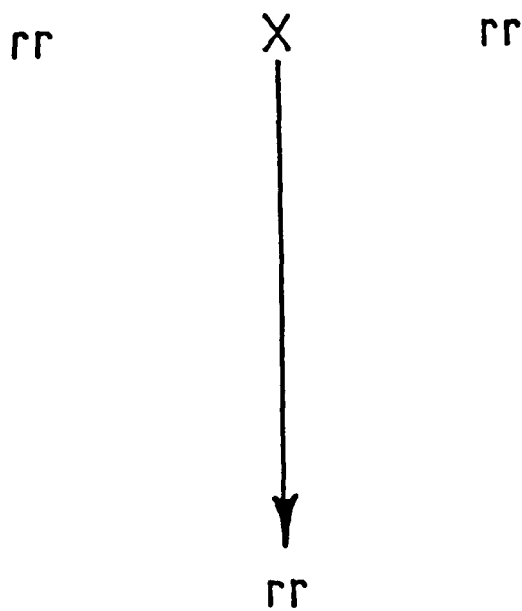

Referring to FIG. 1, (RR) means homozygous resistance; (Rr) means heterozygous resistance; (rr) means homozygous sensitive.

The present invention includes, in a first embodiment, the introduction of a dominant marker gene conferring resistance to a phytotoxic chemical into the male parent of a hybrid cultivar (RR). Both parents are self-compatible or one parent only is self-incompatible. To maximize the efficiency of the approach the male parent should be homozygous for such a gene. In this embodiment, all the true hybrid seed harvested from the female parent (rr) after uncontrolled pollination of the female parent (rr) would be heterozygous for the dominant marker gene and be resistant to the corresponding phytotoxic chemical. If the hybrid seed crop is sprayed at the seedling stage with the appropriate chemical, only seedlings arising from the true hybrid seed (Rr) will survive, and any seedlings arising from contaminating pollen will be eliminated.

The production of a true hybrid seed (Rr) is represented by the path illustrated in (A) of FIG. 1. Seed produced by contaminating pollen (rr) is illustrated in (B) of FIG. 1. Hybrid seed is usually predominantly of true $F_1$ origin, with varying proportions of contaminating seed. Contaminating seed can be eliminated on the basis of sensitivity to a phytotoxic chemical.

After harvest of seed from the female parent in a hybrid seed block, a small seed sample (e.g. 1000 seeds) can be treated with the appropriate chemical, or germinated and the seedlings sprayed with the appropriate chemical, to determine the percent contamination. Recommendations can then be made for the required increase in sowing rates to counter the proportion of contaminating seedlings that will be subsequently eliminated.

Figure 2:
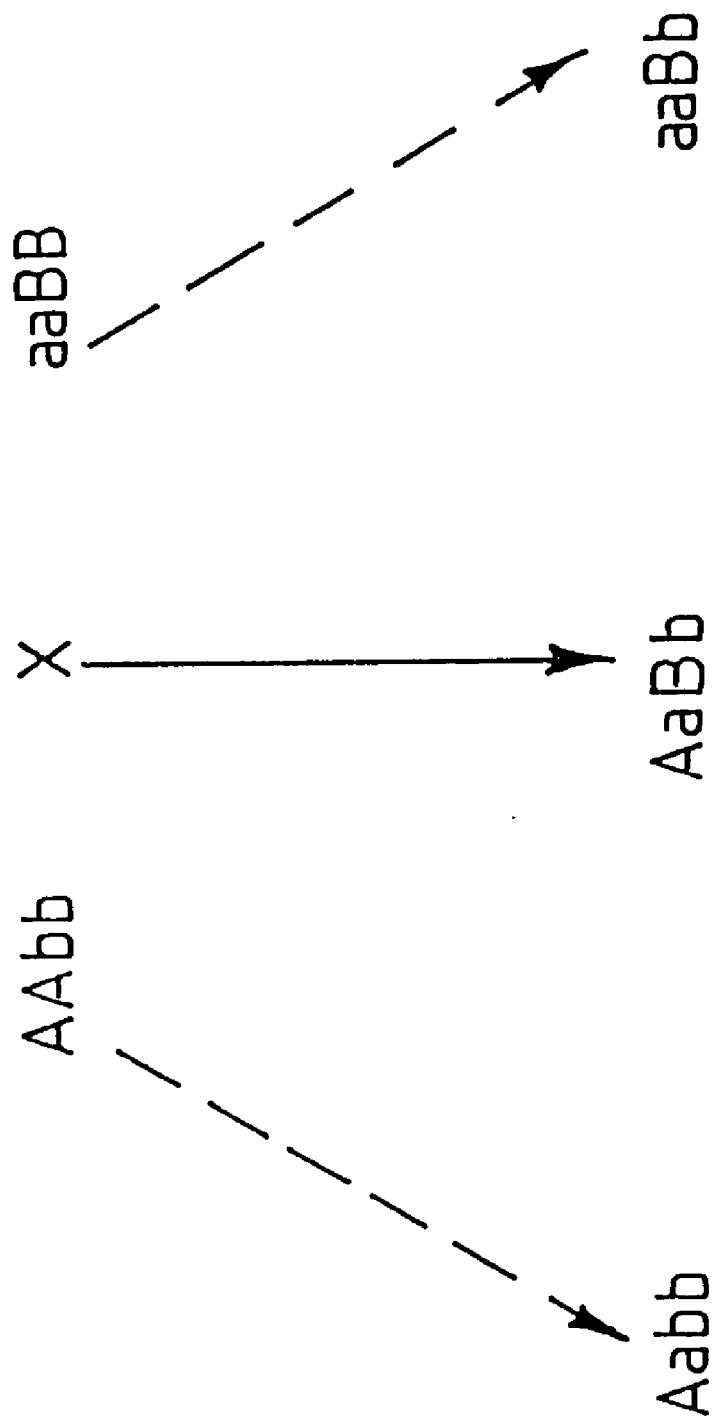
FIG. 2 is a diagrammatic representation of the use of resistance to phytotoxic chemicals for hybrid seed production, according to a second embodiment of the invention.

Referring to FIG. 2, in a second embodiment of the invention self-incompatibility in both parents is used for hybrid seed production and seed is harvested off both parents after uncontrolled pollination of both parents is permitted.. Each parent must therefore be homozygous for different chemical resistance markers. Hybrid seedlings must then be sprayed with both corresponding chemicals to eliminate seedlings arising from contaminating pollen.

The first parent (AAbb) is resistant to the chemical A, the second parent (aaBB) is resistant to the chemical B. Pure hybrid seeds (AaBb) will be resistant to both chemicals A and B. Non-hybrid seed, arising from contaminating pollen (Aabb or aaBb) will carry a resistance to only chemical A or chemical B.

Because the methods of this invention include the step of eliminating non-hybrid seed after hybrid seed production, there is far less need to isolate plots of the parent plants from contaminating pollen sources. These methods allow hybrid seed production to be more efficient. Also many excellent female parents previously unable to be used for commercial hybrid seed production due to irregular reversion to male fertility can now be employed.

Provided germplasm sources are available, conventional plant breeding approaches can be used to transfer resistance to phytotoxic chemicals into male parents or hybrids. Resistance genes can be added directly to specific plant genotypes by exploiting recent advances in plant cell genetics. The applications of somatic cell selection, protoplast fusion and transformation have allowed the genetic manipulation of plants for resistance to specific chemicals (Conner and Meredith, Genetic Manipulation of Plant Cells, *The Biochemistry of Plants. A comprehensive treatise* Vol. 15, Molecular Biology, (1989)).

In most instances such techniques result in individual plants heterozygous for resistance, which must be self-pollinated, then the progeny tested, to generate homozygotes. Although genes for resistance to any phytotoxic chemicals could be used, the most useful approach would involve genes for resistance to herbicides. Agrobacterium-mediated transformation offers an especially convenient method, since several potentially useful genes have been cloned and confer resistance to specific herbicides when integrated into plants.

The production of herbicide resistant plants via transformation may induce glyphosate resistance (Shah et al, Engineering Herbicide Tolerance in Transgenic Plants, *Science*, Vol. 233, (1986); Comai et al, *Nature*, Vol. 317 (1985); U.S. Pat. No. 4,535,060 (Comai) ; Fillatti et al, *Bio/Technology*, Vol. 5 (1987)) or chlorsulfuron resistance (Haughn et al, *Molecular and General Genetics*, Vol. 211, (1988)); or phosphinothriun/bialaphos resistance (De Block, *The EMBO Journal*, Vol 6 (1987)).

EXAMPLE 1

The use of dominant marker genes with resistance to a phytotoxic chemical for circumventing foreign pollen contamination during the production of hybrid seed is illustrated in *Nicotiana plumbaginifolia* plants resistant to kanamycin.

A. Testing for Kanamycin Resistance

Kanamycin resistance can be conveniently studied in *N. plumbaginifolia* by screening for seedlings with green cotyledons (kanamycin-resistant) versus white cotyledons (kanamycin-sensitive), growing in the presence of kanamycin. Seeds were soaked overnight in 1 mM gibberellic acid, surface sterilised with 3% sodium hypochlorite for 5 min. and rinsed thoroughly in sterile distilled water. They were then sown on ½ MS salts (Murashige and Skoog, A Revised Medium for Rapid Growth and Bioassays With Tobacco Tissue Culture, *Physiologia Plantarum*, Vol. 15, (1962)) plus 0.8% agar, supplemented with 300 mg/L kanamycin.

The culture media was autoclaved for 20 min at 121 kPa, with filter sterilised kanamycin being added after autoclaving. Germinating seedlings were incubated at 26° C. under cool white fluorescent light (100 umol. $m^{-2}.sec^{-1}$; 16 h light; 8 h dark daily). Green versus white seedlings can be screened after 7 to 10 days.

Using this approach a single green kanamycin resistant seedling of *N. plumbaginifolia* was observed among many thousands of white kanamycin-sensitive seedlings. This seedling was transferred to a kanamycin-free medium. After 8 weeks it was transferred to soil. Controlled pollinations were made at flowering and the resulting progeny screened for kanamycin resistance.

The original isolated seedling (NpKR) was heterozygous at a single locus for spontaneous mutation to kanamycin resistance. This is evident from the self-pollinated and backcrossed progeny segregating 3:1 and 1:1 respectively for kanamycin resistant and sensitive seedlings (Table 1). From the self-pollinated progeny a single plant (NpKR B) was identified that bred true for kanamycin resistance (Table 1). Clearly, this plant was homozygous at a single locus for kanamycin resistance.

B. Hybrid Seed Production

Hybrid seed production was simulated using a wild-type *N. plumbaginifolia* plant as the female parent and NpKR B (homozygous for kanamycin resistance) as the male parent. Three levels of control over foreign pollen contamination were created by pollinating the emasculated the female parent with:

1. pollen from NpKR B only (tight control),
2. pollen primarily from NpKR B, with a small amount from a wild-type plant (relaxed control), and
3. substantial amounts of pollen from both NpKR B and a wild-type plant (loose control).

TABLE 1

Inheritance of kanamycin resistance in a spontaneous kanamycin-resistant mutant of *Nicotiana plumbaginifolia* (Np KR). Seedling progeny were screened for resistance to 300 mg/L kanamycin

| Cross | Number of seedlings | | Ratio | Chi |
|---|---|---|---|---|
| (female × male) | Green[a] | White[b] | tested | square |
| Wild-type (selfed) | 0 | 1,165 | — | — |
| NpKR (selfed) | 1,150 | 367 | 3:1 | 0:53 |
| Wild-type × NpKR | 292 | 266 | 1:1 | 1:21 |
| NpKR × Wild-type | 256 | 281 | 1:1 | 1:16 |
| NpKR B (selfed) | 808 | 0 | — | — |

[a]kanamycin-resistant
[b]kanamycin-sensitive

When NpKR B is used to pollinate flowers of wild-type plants with these varying levels of pollination control, green kanamycin-resistant true F1 hybrid seedlings can be readily distinguished from the white kanamycin-sensitive seedlings arising from the "foreign" wild-type pollen (Table 2). As expected, the percent of contaminating seed increases as the control over foreign pollen is relaxed. This experiment demonstrates the principle of eliminating non-hybrid seeds when there is the threat of pollen contamination during hybrid seed production.

EXAMPLE 2

The use of dominant marker genes with resistance to a phytotoxic chemical for circumventing self-pollination in the female parent during the production of hybrid seed is illustrated by *Nicotiana plumbaginifolia* plants genetically engineered for resistance to kanamycin.

A. Transformation

A binary vector system involving *Agrobacterium tumefaciens* (strain LBA 4404) harbouring the plasmid pKIWI 6 was used for transformation. This plasmid contains between the left and right borders of the T-DNA, 2 chimeric genes capable of being expressed in plant cells. One confers resistance to the antibiotic kanamycin and consists of the coding region from the neomycin phosphotransferase II gene (from the bacterial transposon Tn5) under the control of the octopine synthase promoter and poly A signal (OCS-NPTII-OCS). The other confers chloramphenicol acetyl transferase (CAT) activity and consists of the coding region of CAT (from bacterial transposon Tn9) under the control of the mannopine synthase promoter and octopine synthase poly A signal.

TABLE 2

The use of kanamycin resistance to eliminate seed arising from contaminating pollen during hybrid seed production in *Nicotiana plumbaginifolia*. Female parent = wild-type kanamycin sensitive plant with varying levels of self-pollination. Male parent = NpKR B (homozygote for kanamycin resistance). Seedling progeny screened for resistance to 300 mg/L kanamycin

| Control over foreign pollen contamination[a] | Number of seeds screened | Percent true F1 hybrid seed[b] | Percent of contaminating selfed seed[c] |
|---|---|---|---|
| Tight | 341 | 100 | 0 |
| Relaxed | 273 | 86 | 14 |
| Loose | 229 | 57 | 43 |

[a]see above
[b]green surviving seedlings, heterozygous for kanamycin resistance
[c]white dying seedlings, sensitive to kanamycin.

Leaf segments from in vitro plants of *N. plumbaginifolia* were dipped in a suspension of *A. tumefaciens* (an overnight culture in MG/L broth—Garfinkel and Nester, *Agrobacterium tumefaciens* Affected in Crown Gall Tumourigenesis and Octopine Metabolism, *Journal of Bacteriology*, Vol. 144, (1980)), blotted dry and cultured on RMOP medium (Sidorov et al, Isoleucine-requiring Nicotiana Plant Deficient in Threonine Deaminase, *Nature*, Vol. 294 (1981)). After 2 days the leaf segments were transferred to the same medium supplemented within 500 mg/L cefotaxime (to prevent Agrobacterium overgrowth) and 300 mg/L kanamycin (to select for transformed plant cells). Regenerated kanamycin-resistant shoots were rooted on MS salts (Murashige & Skoog, 1962) plus 3% sucrose and 0.8% agar, then transferred to soil. Controlled pollinations were made at flowering, and the resulting progeny screened for kanamycin resistance, as described in Example 1.

B. Testing for Kanamycin Resistance

Inheritance of kanamycin resistance can be conveniently studied in *N. plumbaginifolia* by screening for seedling with green cotyledons (kanamycin-resistant) versus white cotyledons (kanamycin-sensitive), 7–10 days after sowing on medium containing 300 mg/L kanamycin. Inheritance was studied in 10 transformed plants; results from only one of these plants (NpT 17) is reported here.

The original transformed plant of NpT 17 was heterozygous for insertion into a single locus of the kanamycin-resistant genes. This is evident from the self-pollinated and backcrossed progeny segregating 3:1 and 1:1 respectively for kanamycin resistant and sensitive seedlings (Table 1). From the self-pollinated progeny a single plant (NpT 17 D) was identified that bred true for kanamycin resistance (Table 3). Clearly, this plant was homozygous at a single locus for kanamycin resistance.

NpT 17D was backcrossed to the wild-type in order to generate a large population of seedlings (over 5,000) heterozygous for inserted kanamycin resistant genes. Any genetic instability of kanamycin resistance would be recognised by the appearance of rare, white, kanamycin-sensitive seedlings within such a population. All the seedlings proved to be kanamycin resistant (Table 3), indicating high genetic stability. Therefore genes with resistance to phytotoxic chemicals, introduced into plants via Agrobacterium-mediated transformation, are sufficiently stable to be used as genetic markers to monitor the seed purity of crop cultivars.

C. Hybrid Seed Production

Hybrid seed production was simulated using a wild-type *N. plumbaginifolia* plant as the female parent and NpT 17D (homozygous for kanamycin resistance) as the male parent. Varying levels of control over female pollen contamination were created by emasculating the female parent at different stages of flower development. *N. plumbaginifolia* is cleistogamous and flowers self-pollinate just prior to opening of the corolla and development of corolla pigmentation. Three levels of control over selfing of the female parent were established.

TABLE 3

Inheritance of kanamycin resistance in a transformed plant of *Nicotiana plumbaginifolia* (NpT 17). Seedling progeny were screened for resistance to 300 mg/L kanamycin.

| Cross (female × male) | Number of Seedlings | | Ratio tested | Chi square |
|---|---|---|---|---|
| | Green[a] | White[b] | | |
| Wild-type (selfed) | 0 | 1,693 | — | — |
| NpT 17 (selfed) | 409 | 141 | 3:1 | 0:12 |
| Wild-type × NpT 17 | 586 | 552 | 1:1 | 1:02 |
| NpT 17D (selfed) | 1,240 | 0 | — | — |
| NpT 17D × Wild-type | 5,339 | 0 | — | — |

[a]kanamycin-resistant
[b]kanamycin-sensitive 1. tight control was exerted by emasculation of flower buds 2–3 cm long, well before pollen is shed, 2. relaxed control was exerted by emasculation of flower 4–5 cm long, just at the point of reaching maximum corolla length and when pollen is beginning to be shed, and 3. loose control was exerted by "emasculation" after corolla pigment development and just as flowers were opening. Considerable self-pollination has occurred by this stage.

When NpT 17D is used to pollinate flowers of wild-type plants with these varying levels of pollination control, green kanamycin-resistant true F1 hybrid seedlings can be readily distinguished from the white kanamycin-sensitive seedlings arising from self-pollination of the female parent (Table 4). As expected, the percent of contaminating seed increases as the control over female selfing is relaxed. This experiment demonstrates the principle of eliminating non-hybrid seeds when there is the threat of pollen contamination from self-pollination of the female parent during hybrid seed production.

Seed of NpKR B (Example 1) NpT 17D (Example 2) and of strain LBA 4404, have been deposited in or are available from the Crop Germplasm Resource Centre, Crop Research Division, DSIR, Private Bag, Christchurch, New Zealand. It is available on request from the curator of the collection.

TABLE 4

The use of kanamycin resistance to eliminate seed arising from self-pollination of the female parent in *Nicotiana plumbaginifolia*. Female parent = wild-type kanamycin sensitive plant with varying levels of self-pollination. Male parent = NpT 17D (homozygote for kanamycin resistant). Seedling progeny screened for resistance to 300 mg/L kanamycin

| Control over self pollination of parent[a] | Number of seeds screened | Percent true F1 hybrid seed[b] | Percent of contaminating selfed seed[c] |
|---|---|---|---|
| Tight | 3,110 | 100 | 0 |
| Relaxed | 3,854 | 92 | 8 |
| Loose | 6,039 | 43 | 57 |

[a]see above
[b]green surviving seedlings, heterozygous for kanamycin resistance
[c]white dying seedlings, sensitive to kanamycin

We claim:

1. A method of forming a substantially pure $F_1$ hybrid population of plants, said method including:
   (a) planting plots of parent plants in which alternating plots contain plants which are used as the male and female parent plants respectively;
   (b) allowing natural fertilization of said plants to occur;
   (c) harvesting fertilised seed from said plots of plants used as the female parent plant only; and
   (d) dosing fertilised seed harvested in step (c) or seedlings produced from said seed with a phytotoxic chemical; wherein the parent plants used as male parent plants are resistant to a phytotoxic chemical, said resistance being attributable solely to a homozygous dominant nuclear marker gene, said resistant gene being absent from said parent plants used as female parent plants.

2. A method as claimed in claim 1 wherein said phytotoxic chemical is a herbicide.

3. A method as claimed in claim 1 wherein said phytotoxic chemical is an antibiotic.

4. A method as claimed in claim 3 wherein said antibiotic is kanamycin.

5. A method as claimed in claim 1 wherein step (d) is carried out before planting said seed.

6. A method as claimed in claim 1 wherein step (d) is carried out after the emergence of seedlings from said seed.

7. A method as claimed in claim 2 wherein step (d) is carried out before planting said seed.

8. A method as claimed in claim 2 wherein step (d) is carried out after the emergence of seedlings from said seed.

9. A method of forming a substantially pure $F_1$ hybrid population of plants in which both parents are self-incompatible or self-compatible, said method including:
   (a) planting plots of parent plants in which alternating plots contain plants used as the first and second parent plants wherein the first parent plants are resistant to a first phytotoxic chemical and have a homozygous dominant nuclear marker gene absent from the second parent plants and wherein the second parent plants are resistant to a second phytotoxic chemical and have a homozygous dominant marker gene absent from the first parent plants;
   (b) allowing natural fertilization of the first and the second parent plants to occur;
   (c) harvesting fertilized seed from the first parent plants and the second parent plants; and
   (d) dosing the harvested fertilized seed or seedlings produced from said seed with both the first and the second phytotoxic chemicals, the resistance to phytotoxic chemicals being attributable in each plant solely to the corresponding homozygous dominant nuclear marker gene, with the gene resistant to the first phytotoxic chemical being absent from the second parent plants and the gene resistant to the second phytotoxic chemical being absent from the first parent plants.

10. A method as claimed in claim 9 wherein the first and the second phytotoxic chemicals are herbicides.

11. A method as claimed in claim 10 wherein the first and the second phytotoxic chemicals are antibiotics.

12. A method as claimed in claim 11 wherein either the first or the second antibiotic is kanamycin.

13. A method as claimed in claim 10 wherein step (d) is carried out before planting said seed.

14. A method as claimed in claim 10 wherein step (d) is carried out after the emergence of seedlings from said seed.

15. A method as claimed in claim 12 wherein step (d) is carried out before planting said seed.

16. A method as claimed in claim 12 wherein step (d) is carried out after the emergence of seedlings from said seed.

17. A method of forming a substantially pure $F_1$ hybrid population of plants in which both parents are self-incompatible or self-compatible, including the steps of:

(a) planting plots of a random mixture of first and second parent plants wherein the first parent plants are resistant to a first phytotoxic chemical and have a homozygous dominant nuclear marker gene absent from the second parent plants and wherein the second parent plants are resistant to a second phytotoxic chemical and have a homozygous dominant marker gene absent from the first parent plants;

(b) allowing natural fertilization of the first and the second parent plants to occur;

(c) harvesting fertilized seed from the first parent plants and the second parent plants; and (d) dosing the harvested fertilized seed or seedlings produced from said seed with both the first and the second phytotoxic chemicals, the resistance to phytotoxic chemicals being attributable in each plant solely to the corresponding homozygous dominant nuclear marker gene with the gene resistant to the first phytotoxic chemical being absent from the second parent plants and the gene resistant to the second phytotoxic chemical being absent from the first parent plants.

18. A method as claimed in claim 17 wherein the first and the second phytotoxic chemicals are herbicides.

19. A method as claimed in claim 18 wherein the first and the second phytotoxic chemicals are antibiotics.

20. A method as claimed in claim 19 wherein either the first or the second antibiotic is kanamycin.

21. A method as claimed in claim 18 wherein step (d) is carried out before planting said seed.

22. A method as claimed in claim 18 wherein step (d) is carried out after the emergence of seedlings from said seed.

23. A method as claimed in claim 20 wherein step (d) is carried out before planting said seed.

24. A method as claimed in claim 20 wherein step (d) is carried out after the emergence of seedlings from said seed.

25. A method of testing the purity of $F_1$ hybrid populations of plants maid method including:

(a) planting plots of parent plants in which alternating plots contain plants used as the male and female parent plants respectively;

(b) allowing natural fertilization of the plants to occur;

(c) harvesting fertilized seed from said plots of plants used as the female parent plant only;

(d) planting a small quantity as a sample of the seeds;

(e) dosing the seedlings after emergence with a phytotoxic chemical, wherein the parent plants used as male parent plants are resistant to said phytotoxic chemical, said resistance being attributable solely to a homozygous dominant nuclear marker gene being absent from the parent plants used as female parent plants; and (f) determining the percentage of seedlings resistant to the phytotoxic chemical.

26. A method of testing the purity of $F_1$ hybrid populations of plants in which both parents are self-incompatible or self-compatible, said method including:

(a) planting plots of parent plants in which alternating plots contain plants used as the first an second parents respectively or a random mixture of first and second parent plants;

(b) allowing natural fertlization of the first and said second parent plants to occur;

(c) harvesting fertilized seed from the first parent plants and the second parent plants;

(d) planting a small quantity as a sample of said seeds;

(e) dosing the seedlings after emergence with a first and a second phytotoxic; chemical with the first parent plants being resistant to the first phytotoxic chemical and the second parent plants being resistant to the second phytotoxic chemical, the resistance being attributable in each plant solely to a homozygous dominant nuclear marker gene with the gene resistant to the first chemical being absent from the second parent plants and the gene resistant to the second chemical being absent from the first parent plants; and (f) determining the percentage of seedlings resistant to the first and the second phytotoxic chemicals.

27. A method of testing the purity of $F_1$ hybrid populations of plants in which both parents are self-incompatible or self-compatible, including the steps of:

(a) planting plots of a random mixture of first and second parents respectively;

(b) allowing natural fertilization of the first and said second parent plants to occur;

(c) harvesting fertilized seed from the first parent plants and the second parent plants;

(d) planting a small quantity as a sample of said seeds;

(e) dosing the seedlings after emergence with a first and a second phytotoxic chemical with the first parent plants being resistant to the first phytotoxic chemical and the second parent plants being resistant to the second phytotoxic chemical, the resistance being attributable in each plant solely to a homozygous dominant nuclear marker gene with the gene resistant to the first chemical being absent from the second parent plants and the gene resistant to the second chemical being absent from the first parent plants; and (f) determining the percentage of seedlings resistant to the first and the second phytotoxic chemicals.

* * * * *